United States Patent [19]
Kuczkowski et al.

[11] 3,947,576
[45] Mar. 30, 1976

[54] SYNERGISTIC BIOSTATIC COMPOSITION

[75] Inventors: John S. Kuczkowski, Chicago; William A. Konitz, Kankakee, both of Ill.

[73] Assignee: Mortell Company, Kankakee, Ill.

[22] Filed: Sept. 27, 1973

[21] Appl. No.: 401,402

[52] U.S. Cl. .................. 424/263; 424/272; 424/340
[51] Int. Cl.$^2$.. A01N 9/00; A01N 9/22; A01N 9/24; A01N 9/28
[58] Field of Search.................... 424/263, 272, 340

[56] References Cited
UNITED STATES PATENTS
3,445,398   5/1969   Jungermann........................ 424/340

*Primary Examiner*—Jerome D. Goldberg
*Assistant Examiner*—D. W. Robinson
*Attorney, Agent, or Firm*—Wegner, Stellman, McCord, Wiles & Wood

[57] ABSTRACT

A biocidal composition for contact sterilization comprising essentially a vinyl oxozaline fatty or carboxylic acid ester of tris (hydroxymethyl) amino methane having three alkyl groups, each of 1 to about 17 carbon atoms and all alkyl groups being the same or different and two different biocide compositions combined or reacted with the ester. The disclosure also includes biocidal materials, such as paints, toiletries, coating compositions, sterilizing compositions, adhesive-sealant compositions, pharmaceutical compositions, and similar products having as an active ingredient the above biocidal composition and a compatible carrier material.

4 Claims, No Drawings

SYNERGISTIC BIOSTATIC COMPOSITION

Biocidal compositions for contact sterilization are well known and much has been published on the composition and uses. The composition of this invention, however, has a number of advantages that are superior to those of prior compositions of which applicants are aware in that the active ingredients have low toxicity to animals and the composition is easily made, is active even in small proportions, and is stable while exerting its biocidal properties. One of the features of this invention, therefore, is to provide an improved biocidal composition, as disclosed above, and employing the above ester in combination with two biocides of the class consisting of 2,3,5,6 Tetrachloro 4, (methylsulfonyl) pyridine; and 2,4,4 Trichloro-2-Hydroxydiphenyl ether.

The ester has the probable structural formula

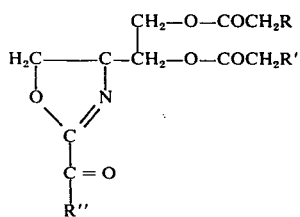

in which R, R', and R'' are the same or different alkyl groups, with each having fron one to about 17 carbon atoms and the two biocides may be any pair selected from the above class. Although the invention is not limited by any theory, either stated or implied herein, it is believed that these three components form a closed triangle. It is also believed that each biocide links with the TA-100 as an alkyl group to give an exposed electron for linking with the other biocide.

The vinyl oxozaline fatty or carboxylic acid ester of tris (hydroxymethyl) amino methane having three alkyl groups is sometimes identified herein as TA-100. It is present in the three-component biocidal composition (synergistic solution) in an amount of about 25-55%. One of the two biocides is present in the amount of about 29-69%, and the other in the amount of about 6-16%, for a total of 100%. All percentages herein are by weight. It is believed that the two biocides combine or react with the TA-100 by addition with the alkyl groups or possibly by electrophylic substitution. It has the effect of forming a three-member complex with an inhibitory and, even, a killing action against bacteria and fungi to provide contact sterilization.

The TA-100, when complexed as described with the two biocides, results in a biocidal composition having increased effectiveness over the sum of the effectiveness of the two biocides added together. In other words, the TA-100 acts as a true synergist, even though it has no cidal activity toward bacteria of its own. Furthermore, the biocidal activity of the resulting three-component complex is directly proportional to the amount of the TA-100 ester and with synergistic activity being noted so long as the amount is at least 20% of the complex composition, although, as stated above, the preferred minimum amount is about 25%.

In the above ranges of amounts of the three components in the complex, it should be understood that a composition having biocidal characteristics could be produced outside these ranges of amounts but for practical reasons these ranges are preferred.

The TA-100 ester can be generally classified as the reaction product of an amino compound, an organic carboxylic acid, and an aldehyde. The chemical combination or reaction of the TA-100 with the two biocides creates a synergistic complex which is believed to be of closed structure and has the ability to impregnate the systems carrier so as to achieve a homogeneous distribution throughout the system, thereby increasing the biocidal surface that acts as a barrier to microbial attack.

The biocidal composition which is effective as a fungicide and bacteriocide is usable in sterilizing compositions, paints, surface coating materials such as plastics, cosmetics, soaps, salves, ointments, deodorants, lotions, shampoos, skin creams, and pharmaceuticals such as gargles and sterilizing sprays when employed with the customary carriers, such as ointment bases, and thus find very effective use in coatings, tile sealant, air filter protective sprays, vinyl cover adhesives, protective floor coverings, and in grout mixes. Although the biocidal composition is usable with water-based systems of pH 4-9, it is also usable with oils or resinous organic liquid bases.

In order to prepare the biocidal composition, the mixture of TA-100 and the two biocides is mixed with high shear and at the temperature, in the area of room temperature or above at which time the solubility and the complexing of the compounds is effected.

The following examples illustrate the invention:

EXAMPLE NO. 1

| | |
|---|---|
| TA-100 (oxozaline ester) | 25% |
| 2,3,5,6 Tetrachloro 4, (methylsulfonyl) pyridine | 69% |
| 2,4,4 Trichloro-2-Hydroxydiphenyl ether | 6% |

EXAMPLE NO. 2

| | |
|---|---|
| Water | 16.0% |
| Igepal CO630 (nonylphenoxy poly(ethyleneoxy) ethanol) | 4.5% |
| Rohm & Haas Tamol 731 (Sodium salt of polymeric carboxylic acid) | 3.0% |
| 2,3,5,6 Tetrachloro 4, (methylsulfonyl) pyridine | 44.5% |
| 2,4,4 Trichloro-2-Hydroxydiphenyl ether | 7.0% |
| TA-100 (oxozaline ester) | 25.0% |

This is a biostatic concentrate formula preferred for use in water-reduced coatings.

The above compositions may be used as such or may be added directly to completed pigmented coating materials as concentrates or they can be included in the formula during manufacture of pigmented coating materials. The amount of the biocidal composition three-component complex used in the formulas can be any amount desired but, ordinarily, will be from about 0.5% to about 10% by weight of the formulation.

Examples of such formulations are as follows:

EXAMPLE NO. 3

A coating primer for providing a microbial control coating on a solid surface has the following ingredients:

| | |
|---|---|
| Alkyd Resin (glycerol, phthalic anhydride, linseed oil) | 37.59% |
| Mineral Spirits (hydrocarbon solvent) | 14.28% |
| TiO$_2$ | 14.83% |
| Magnesium Silicate | 23.48% |
| Zinc Oxide | 7.32% |
| Hydrolized Clay (AL$_2$O$_3$ SiO$_2$) | 0.36% |
| Methyl Alcohol | 0.18% |
| TA-100 (oxozaline ester) | 0.66% |
| 2,3,5,6 Tetrachloro 4, (methylsulfonyl) | 0.07% |

-continued

| | |
|---|---|
| pyridine 2,4,4 Trichloro-2-Hydroxydiphenyl ether | 0.02% |
| Dimethyl Formamide | 0.74% |
| Cobalt Naphthenate | 0.18% |
| Zirconium Naphthenate | 0.09% |
| Manganese Naphthenate | 0.09% |
| Anti-skin Agent (methylethyl ketoxime, or dry compound of this class) | 0.09% |
| | 100.00% |

EXAMPLE NO. 4

A semi-gloss coating with biocidal characteristics has the following formula:

| | |
|---|---|
| Methocel Liquid or organic thickener | 12.50% |
| Tamol 731 (sodium salt of polymeric carboxylic acid) | 0.68% |
| Igepal CO630 (nonylphenoxy poly(ethyleneoxy) ethanol) | 0.16% |
| Hercules 257 Defoamer (a blend of mineral oils and silicone derivatives) | 0.16% |
| Propylene Glycol | 7.39% |
| DB Acetate (Diethylene glycol monobutyl ether acetate) | 1.32% |
| TA-100 (oxozaline ester) | 1.51% |
| The biocide of Example No. 5 | 5.68% |
| TiO$_2$ | 27.28% |
| Water | 5.68% |
| Ucar 380 (acrylic polyvinyl acetate copolymer) | 37.53% |
| Hercules 257 Defoamer (a blend of mineral oils and silicone derivatives) | 0.09% |
| Carbon Black Dispersion | 0.01% |
| Phthalocyanine Blue Tint Dispersion | 0.01% |
| | 100.00% |

In preparing the above formulation, the ingredients were mixed in a high speed disperser, such as a Cowles Dissolver (a trademark of the Morehouse-Cowles Corporation), by first adding the liquid of the first ingredient and then adding the listed ingredients through the titanium dioxide, while stirring from 30 minutes to 1 hour at high speed to provide a dispersing action. Then, the remaining ingredients were added at a lower speed over a period of 20 minutes.

EXAMPLE NO. 5

An example of a biocidal synergistic composition has the following ingredients:

| | |
|---|---|
| Water | 16.90% |
| Igepal CO630 (nonylphenoxy poly(ethyleneoxy) ethanol) | 2.98% |
| Igepal CTA-639 (alkyl phenoxy poly(ethyleneoxy) ethanol) | 1.49% |
| Tamol 731 (sodium salt of polymeric carboxylic acid) | 2.98% |
| TA-100 (oxozaline ester) | 25.22% |
| SA-1013 Biocide (2,3,5,6 Tetrachloro 4, (methylsulfonyl) pyridine) | 44.65% |
| Geigy (2,4,4 Trichloro-2-Hydroxydiphenyl ether) | 5.78% |
| | 100.00% |

The ingredients down through Tamol 731 were mixed for 5 minutes in a Cowles tank, then the TA-100 was added and mixed for an additional 10 minutes and, finally, the last two ingredients were sifted into the tank and mixed for about 15 minutes until well-dispersed in the other ingredients to provide a substantially homogeneous composition.

EXAMPLE NO. 6

In this example, there is produced a flat paint having excellent washability characteristics. This formulation has the following ingredients:

| | |
|---|---|
| Water | 19.85% |
| Methocel (hydroxypropyl ethyl cellulose) | .41% |
| Ammonium Hydroxide | .04% |
| K.T.P.P. (potassium tripoly phosphate) | .18% |
| Propylene Glycol | 5.28% |

-continued

| | |
|---|---|
| Colloid 677 (siliconized hydrocarbon oil | .06% |
| Igepal CO630 (nonylethoxy poly(ethyleneoxy)ethanol | .37% |
| TiO$_2$ | 20.21% |
| Asbestine (Magnesium silicate) | .97% |
| Minex No. 7 (Aluminum silicate) | 9.34% |
| The biocide liquid of Example No. 5 | 2.39% |
| Water | 9.77% |
| Airflex A-720 (vinyl acrylic, ethylene terpolymer) | 31.13% |
| | 100.00% |

In preparing this material, the water was added to the clean Cowles tank. Then, the methocel was sifted slowly into the water together with the ammonium hydroxide to dissolve the methocel, and the whole was mixed for about 20 minutes. Then, the K.T.P.P. and following-listed ingredients, through the titanium dioxide pigment were added and the speed of mixing was increased to provide a dispersing action and this was continued for about 30 minutes. At the end of this time, the additional water was added slowly at low speed and, finally, the remaining ingredients were added slowly at the lowest speed and the whole was mixed for an additional 20 minutes.

We claim:

1. A biocidal complex for contact sterilization prepared by thoroughly mixing together about 25–55% of a vinyl oxozaline fatty or carboxylic acid ester of tris-(hydroxymethyl)-amino-methane of the formula:

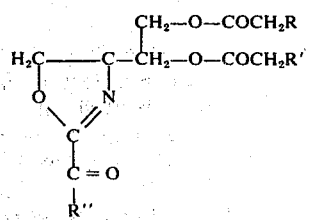

where R, R' and R'' are the same or different alkyl groups each of 1 to 17 carbon atoms, and about 29–69% of the biocide 2,3,5,6-Tetrachloro-4-(methylsulfonyl)-pyridine and about 6–16% of the biocide 2,4,4-Trichloro-2-Hydroxydiphenyl ether for a total of 100%.

2. A biocidal composition with a pH of about 4–9 having as an active ingredient the biocidal complex of claim 1 and a compatible carrier material comprising water.

3. A biocidal sterilizing composition having as an active ingredient the biocidal complex of claim 1 and a compatible carrier material.

4. A biocidal complex for contact sterilization prepared by thoroughly mixing together about 25–55% of a vinyl oxozaline fatty or carboxylic acid ester of tris-(hydroxymethyl)-amino-methane of the formula:

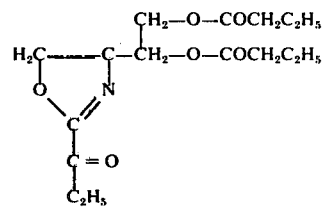

and about 29–69% of the biocide 2,3,5,6 Tetrachloro-4,-(methylsulfonyl)-pyridine and about 6–16% of the biocide 2,4,4-Trichloro-2-Hydroxydiphenyl ether for a total of 100%.

* * * * *

UNITED STATES PATENT AND TRADEMARK OFFICE
CERTIFICATE OF CORRECTION

PATENT NO. : 3,947,576
DATED : March 30, 1976           Page 1 of 2
INVENTOR(S) : John S. Kuczkowski & William A. Konitz It is certified that error appears in the above-identified patent and that said Letters Patent are hereby corrected as shown below:

In the specification, column 1, lines 21-29, delete the structural formula and insert the following structural formula in lieu thereof:

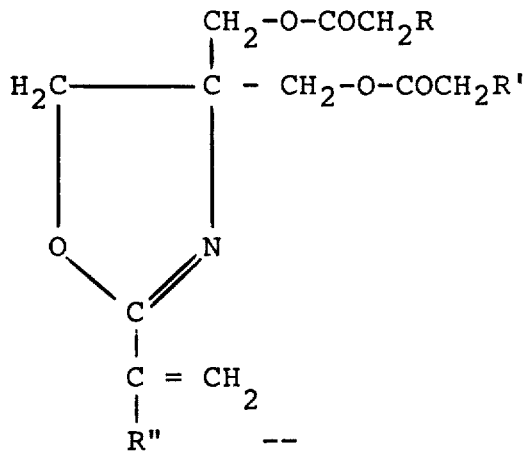

In claim 1, column 4, lines 56-63, delete the structural formula and insert the following structural formula in lieu thereof:

UNITED STATES PATENT AND TRADEMARK OFFICE
CERTIFICATE OF CORRECTION

PATENT NO. : 3,947,576
DATED : March 30, 1976
INVENTOR(S) : John S. Kuczkowski & William A. Konitz It is certified that error appears in the above-identified patent and that said Letters Patent are hereby corrected as shown below:

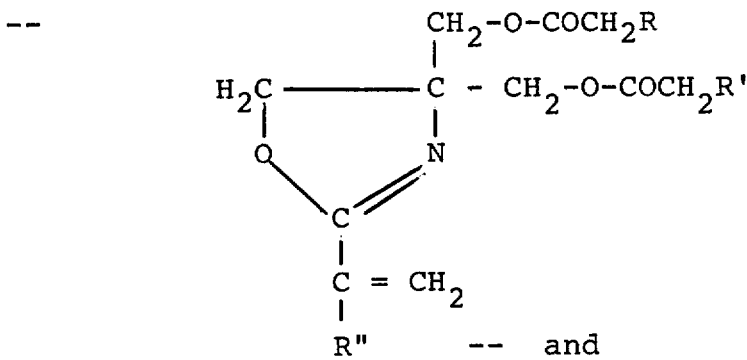

In claim 4, column 6, lines 1-9, delete the structural formula and insert the following structural formula in lieu thereof:

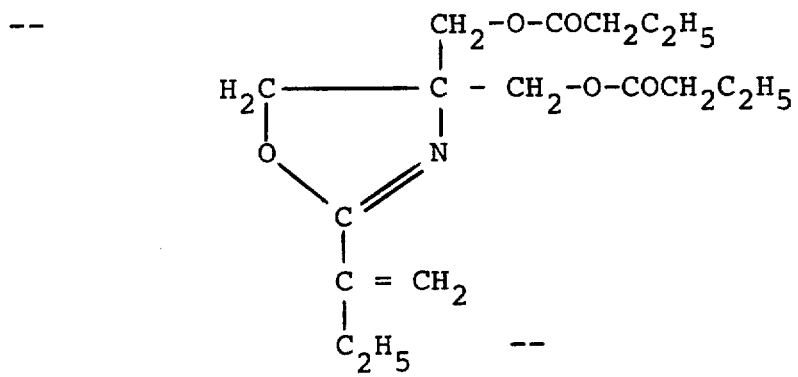

Signed and Sealed this

Third Day of May 1977

[SEAL]

Attest:

RUTH C. MASON
Attesting Officer

C. MARSHALL DANN
Commissioner of Patents and Trademarks